United States Patent [19]

Canfield et al.

[11] Patent Number: 5,322,858

[45] Date of Patent: Jun. 21, 1994

[54] N,N'-SUBSTITUTED IMIDODICARBONIMIDIC DIAMIDES DERIVED FROM HYDROXYLAMINES

[75] Inventors: Craig Canfield, Boyds, Md.; David P. Jacobus, Princeton; Neil J. Lewis, Plainsboro, both of N.J.

[73] Assignee: Jacobus Pharmaceutical Co. Inc., Princeton, N.J.

[21] Appl. No.: 837,258

[22] Filed: Feb. 14, 1992

[51] Int. Cl.⁵ .................. C07C 279/26; C07C 321/28; A61K 31/155

[52] U.S. Cl. ............................. 514/635; 514/331; 514/428; 514/445; 514/616; 514/630; 514/895; 546/231; 548/566; 549/65; 564/157; 564/220; 564/233; 564/234

[58] Field of Search ............ 564/234, 157, 220, 233; 514/635, 895, 445, 616, 630; 549/65

[56] References Cited

U.S. PATENT DOCUMENTS

| | | | |
|---|---|---|---|
| 3,660,394 | 5/1972 | Mamalis et al. | 544/206 |
| 3,723,429 | 3/1973 | Mamalis et al. | 544/206 |

FOREIGN PATENT DOCUMENTS

| | | |
|---|---|---|
| 1957769 | 9/1970 | Fed. Rep. of Germany. |
| 0603070 | 6/1948 | United Kingdom. |
| 0665680 | 1/1952 | United Kingdom. |
| 1250531 | 10/1971 | United Kingdom. |
| 0667116 | 2/1992 | United Kingdom. |

OTHER PUBLICATIONS

International Search Report, Apr. 22, 1993 (PCT/US93/00395).
Bajwa et al. "The Chemistry of Drugs III, etc." *Heterocycles*, vol. 20, No. 5 (1983) pp. 839–843.
Mamalis et al I. "Amino-oxy-derivatives, etc." *J. Chem. Soc.* (1962) pp. 3915–3926.
Weinberg, "The Anti-Microbial Activity of N¹,N⁵ Substituted Biguanides", Antibiotics & Chemotherapy 11 (1961) pp. 572–582.

*Primary Examiner*—Richard L. Raymond
*Assistant Examiner*—Peter G. O'Sullivan

*Attorney, Agent, or Firm*—Omri M. Behr; Matthew J. McDonald

[57] ABSTRACT

There are provided compounds of the formula

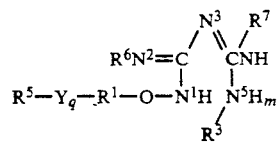

wherein $R^1$ is a substituted or unsubstituted divalent aliphatic group of 1 to 16 carbon atoms; wherein the substituents are mono or poly and are selected from the group consisting of lower alkyl, aryl and arlkyl, $R^3$ is selected from the group consisting of same group of values as $R^5$, $R^5$ is selected from the group consisting of substituted and unsubstituted alkyl of 1–10 carbon atoms, aryl, cycloalkyl and heterocycloalkyl of 3–8 carbon atoms, wherein the substituents are mono or poly and are selected from the group consisting of lower alkyl, cycloalkyl of 3–8 carbon atoms, lower alkenyl, lower alkynyl, nitro, lower alkoxy, lower alkoxycarbonyl, phenyl loweralkyl, phenyl, mono and polyhalophenyl, phenoxy, mono and polyhalophenoxy, $R^6$ and $R^7$ may be the same or different and are hydrogen, alkanoyl or alkoxyalkanoyl, $R^7$ may also have the same value as $R^5$, Y is oxygen or sulfur, m is 0 or 1, q is 0 or 1, wherein the prefix alk designates moieties which are straight chain or branched chain, and the term lower designates 1–6 carbon atoms and the unmodified term alk signifies 1–24 carbon atoms, the respective tautomers thereof, the pharmaceutically acceptable salts and addition salts thereof and the hydrates of said salts and addition salts. There are further provided methods of protecting subjects liable thereto from infections caused by an organism of the group Plasmodium sp., Mycobacterium sp. and Pneumocystis carinii by administering to a subject liable to such infection, a prophylactically effective amount of a compound of the foregoing formula. These compounds will also reduce the level of infection where said subjects have already been infected.

32 Claims, No Drawings

N,N'-SUBSTITUTED IMIDODICARBONIMIDIC DIAMIDES DERIVED FROM HYDROXYLAMINES

BACKGROUND OF THE INVENTION

1. Field of the Invention

This invention relates to N,N'-substituted asymmetrical imidodicarbonimidic diamides derived from hydroxylamines and their derivatives and to processes for making them.

2. Discussion of the prior art.

The related triazine derivatives (Onori, E. and Majori, G. Recent acquisitions on chemotherapy and chemoprophylaxis of malaria. Ann 1st Super Sanita. 25:659–74) (1989) are poorly absorbed and have been shown to be less effective in eliciting cures when administered orally, as compared to injection, to malaria-infected aotus monkeys. The related triazine derivatives, must be administered by injection to observe activity comparable to or exceeding other known antimalarial drugs. (Knight, D. J. and Peters, W. The antimalarial activity of N-benzyloxy dihydrotriazines. I. Ann. Tropical Med. Parasitor. 74:393–404 (1980). The antimalarial activity of N-benzyloxydihydrotriazines. IV. Ann. Trop. Med. Parasitol. 76:9–14, Knight, D. J. and Williamson, P. (1982), U.S. Pat. No. 4,232,022, U.S. Pat. No. 4,179,562). Additionally such triazines have been reported as poorly tolerated when given by the oral route (Knight, D. J. and Williamson, P. (1982) supra).

SUMMARY OF THE INVENTION

There are provided novel, pharmaceutically active compounds of the formula

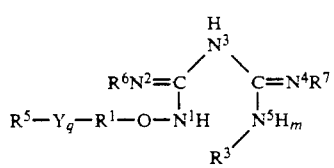

and all of its tautomers such as, for example:

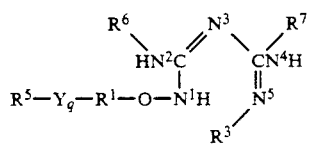

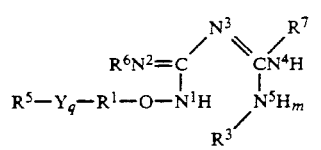

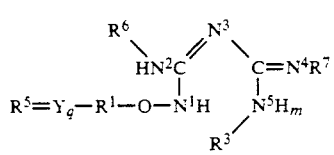

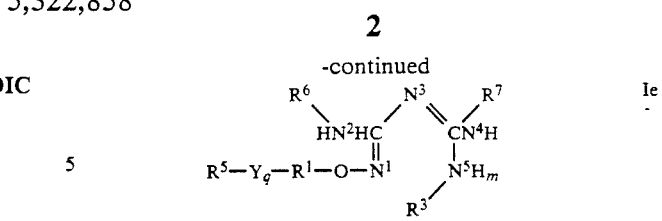

all being subsumed under the general designation of formula I. Any one of these formulae used herein shall be considered as the equivalent of and subsume the others.

In Formula I:

$R^1$ is a substituted or unsubstituted divalent aliphatic group of 1 to 16 carbon atoms; wherein the substituents are mono or poly and are selected from the group consisting of lower alkyl, aryl and aralkyl, $R^3$ is selected from the group consisting of same group of values as $R^5$, and may also form, with the nitrogen to which it is attached a saturated heterocycle of 4–8 carbon atoms, $R^5$ is selected from the group consisting of substituted and unsubstituted alkyl of 1–10 carbon atoms, cycloalkyl, heterocycloalkyl of 3–8 carbon atoms, mono and polycarbocycloaryl of 4–7 atoms per ring, wherein the substituents are mono or poly and are selected from the group consisting of lower alkyl, halo lower alkyl, cycloalkyl of 3–8 carbon atoms, lower alkenyl, lower alkynyl, nitro, lower alkoxy, lower alkoxycarbonyl, phenyl loweralkyl, phenyl, mono and polyhalophenyl, phenoxy, mono and polyhalophenoxy, and halo provided however, that such substitution is in a mono and polycarbocycloaryl of 4–7 atoms per ring, $R^6$ and $R^7$ may be the same or different when $R^6$ is hydrogen, alkanoyl or alkoxyalkanoyl and may also form, with the nitrogen to which they are attached, a saturated heterocycle of 4–8 carbon atoms, $R^7$ may also be selected from the group consisting of same group of values as $R^5$, Y is oxygen or sulfur, m is 0 or 1, q is 0 or 1, provided that unless otherwise stated the prefix alk designates moieties which are straight chain or branched chain, and the term lower designates 1–6 carbon atoms and the unmodified term alk signifies 1–24 carbon atoms, the pharmaceutically acceptable salts and addition salts thereof and the hydrates of said salts and addition salts, and the mono and diacyl derivatives thereof.

It is believed the chemical formulas and names used herein correctly and accurately reflect the underlying chemical compounds. However, the nature and value of the present invention does not depend upon the theoretical correctness of these formulas, in whole or in part. Thus, it is understood that the formulas used herein, as well as the chemical names attributed to the correspondingly indicated compounds, are not intended to limit and do not limit the invention in any way, including restricting it to any specific tautomeric form or to any specific optical or geometric isomer.

Compounds within the scope of the present invention have antimicrobial and antiparasitic activity of various kinds, including antimalarial activity and provide a novel pharmacological activity since unlike previously reported triazine derivatives the parent compound and its derivatives described herein are highly bioavailable by virtue of their ability to be readily absorbed when taken orally.

There is disclosed a method for synthesizing the novel compounds of the present invention by reacting an appropriately substituted hydroxylamine, thioamine or isosteric amine with a substituted dicyanodiamide in the presence of an acid catalyst to form a disubstituted imidodicarbonimidic diamide with N and N' substituents. These products may then be further salified or further reacted to produce additional substituents in the biguanide.

The aforesaid substituted hydroxylamines may be synthesized as follows:

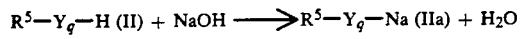

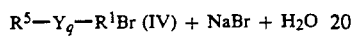

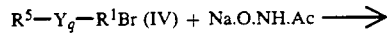

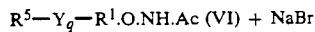

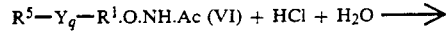

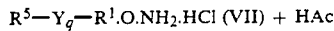

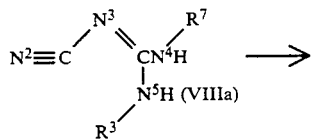

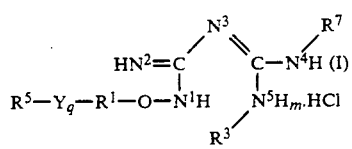

The foregoing route is valid where $Y_q$ is O or S and $R^7$ is hydrogen, alkanoyl or alkoxyalkanoyl. However where $R^7$ is selected from the $R^5$ group a different route is desirable to compound (VII) and then to (I).

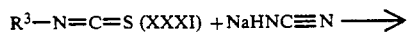

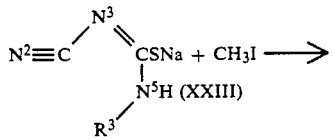

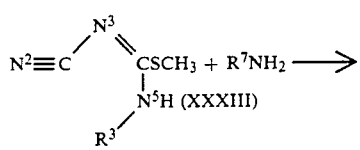

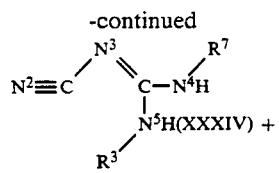

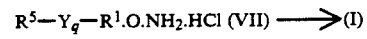

Thus there are also provided methods of protecting subjects liable thereto, from infections caused by an organism selected from the group consisting of Plasmodium sp., Mycobacterium sp and Pneumocystis carinii which comprises administering to a subject liable to infection by exposure to such organisms, a prophylactically effective amount of a compound of the above formula I. Similarly there are provided methods of reducing the level of infection in subjects suffering from infections caused by an organism selected from the foregoing group which comprise administering to such subjects an effective amount of a compound of formula I.

Prophylactic and treatment compositions for the foregoing purposes are also provided which comprise a prophylactically or infection reductively effective amount of a compound of formula I and a pharmaceutically acceptable carrier. Such compositions may be formulated for oral administration by which route these compounds and compositions are well absorbed, especially as tablets or capsules.

DESCRIPTION OF THE PREFERRED EMBODIMENTS

There are provided pharmaceutically active compounds of the formula

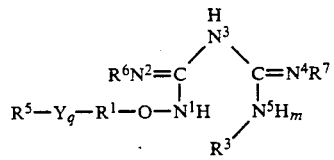

wherein:

$R^1$ is substituted or unsubstituted divalent aliphatic group of 1 to 16 carbon atoms, suitably lower alkyl such as methyl, ethyl, n-propyl, iso-propyl, isobutyl, n-pentyl, n-decyl, or cycloalkyl such as cyclopentyl, cyclohexyl, cycloheptyl.

The substituents are mono or poly and are selected from the group consisting of lower alkyl such as methyl, ethyl, n-propyl, iso-propyl, isobutyl, n-pentyl, n-decyl, or cycloalkyl such as cyclopentyl, cyclohexyl, cycloheptyl, aryl, suitably phenyl, napthyl, tetrahydronapthyl, indanyl, indenyl, benzofuranyl, benzopyranyl, and aralkyl such as benzyl and phenethyl, $R^3$ is selected from the group consisting of same group of values as $R^5$, if desired it may also form, with the nitrogen to which it is are attached, a saturated heterocycle of 4-8 carbon atoms such as pyrrolino, piperidinocer pyrrolidino, $R^5$ is selected from the group consisting of substituted and unsubstituted alkyl of 1-10 carbon atoms such as methyl, ethyl, n-propyl, iso-propyl, isobutyl, n-pentyl, n-decyl, or cycloalkyl such as cyclopentyl, cyclohexyl, cycloheptyl, aryl, suitably phenyl, naphthyl, tetrahydronaphthyl, indanyl, indenyl, benzofuranyl, benzopyranyl, biphenylyl, heterocycloalkyl such as tetrahydrofuranyl, pyrrolidinyl, piperidyl and morpholinyl, wherein the substituents are mono or poly and are selected from the group consisting of lower alkyl, such as methyl, ethyl, n-propyl, iso-propyl, isobutyl, n-pentyl, halo lower alkyl such as trifluoromethyl or cycloalkyl such as cyclopentyl, cyclohexyl, or cycloheptyl, lower alkenyl, such as ethenyl, n-propenyl, iso-propenyl, isobutenyl, n-pentenyl, lower alkynyl, such as ethynyl, n-propynyl, iso-propynyl, isobutynyl, n-pentynyl, nitro, lower alkoxy, such as methoxy, ethoxy, n-propoxy, iso-propoxy, isobutoxy, n-pentoxy, lower alkoxycarbonyl, such as formyloxy, acetoxy, propionyloxy, and butyryloxy, phenyl loweralkyl, such as benzyl, phenyl phenoxy, mono and polyhalophenyl, mono and polyhalophenoxy, wherein the halo group is fluoro, chloro or bromo, which may also serve as mono and poly substituents for the above named aryl moieties.

$R^6$ and $R^7$ may be the same or different and are hydrogen or alkanoyl, suitably formyl, acetyl, propionyl, and butyryl. If desired they may also form, with the nitrogen to which they are attached a saturated heterocycle of 4–8 carbon atoms such as pyrrolidyl, piperidinyl or pyrrolidinyl.

Y is oxygen or sulfur.

m is 0 or 1.

q is 0 or 1, the pharmaceutically acceptable salts and addition salts thereof and the hydrates of said salts and addition salts.

Also included are the mono and diacyl derivatives thereof, suitably alkanoyl or aralkanoyl derivatives such as acetyl and benzyl derivatives.

The compounds of formula I of the present invention may be synthesized by a number of routes of which the following is of most general applicability and is preferred. In this multi-step process, some of the intermediates may be commercially available, however for the sake of completeness, the following process description commences with readily commercially obtainable starting materials.

Where it is intended to form a compound wherein Y is oxygen or sulfur and q is 1, the starting material is an alkanol, a phenol or a mercaptan (II). Where the starting material is an alkanol, there is utilized an excess of the alkanol and the desired quantity to be reacted is treated with one equivalent of alkali metal sodium to form the alkali metal salt in alkanolic solution.

In the case of mercaptans or phenols there is utilized an excess of aqueous alkali, suitably sodium hydroxide, which forms the appropriate sodium salt at ambient temperatures in a few minutes. There is then added an excess, suitably a 2-fold excess of a dihaloalkane over the calculated amount of alkali metal salt, the position of the halo groups determining the length of the $R^1$ moiety. The mixture is heated under reflux for from about 1 to about 4 hours. A further excess of alkali is added and the reaction mixture held at between 50° and 70° C. for about ½ hour. The mixture is cooled, the lower organic layer separated, washed, and distilled under reduced pressure to give water, unreacted dihaloalkane and the desired $R^5$ oxy or thioalkyl halide (IV).

Acetohydroxamic acid is converted into the corresponding alkali metal hydroxamate (V) by addition of alkanoic, suitably an ethanolic solution of alkali metal hydroxide such as sodium or potassium hydroxide. The oxy or thioalkyl halide (IV) produced as above, is then added and the mixture heated under reflux, suitably from about 4 to about 8 hours and cooled. Precipitated alkali metal halide salt is removed by filtration, the solvents removed under reduced pressure and the residue dissolved in a polar, water miscible, organic solvent, suitably acetone solution, again filtered and concentrated under reduced pressure to yield the corresponding oxy or thioalkyl acetohydroxamate (VI).

Where q is 0, for example where $R^5$-$R^1$ is benzyl, the corresponding $R^5$-$R^1$ halo compound (IV) such as benzyl bromide, may be commercially obtained and this is then reacted directly with the alkali metal acetohydroxamate as described above.

The acetohydroxamate (VI) is taken up in an alkanol, to which is added an excess of dilute mineral acid, suitably hydrochloric acid, the mixture heated under reflux for about 2 to about 6, suitably from 4 hours, the solvents removed under pressure and the residue extracted with dry diethyl ether. The solvent is then removed under reduced pressure and the residue recrystallized from an alkanol, suitably ethanol or isopropanol, to give the desired alkyloxyamine hydrochloride (VII).

The alkyloxyamine hydrochloride (VII) is taken up in an alkanol and treated with concentrated aqueous hydrochloric acid until the solution is clearly acidic. The appropriate omega-substituted dicyandiamide, for example, a lower alkyl dicyandiamide (VII), is added in excess. The mixture heated under reflux for about 2 to about 6 hours, the solvents removed by evaporation under reduced pressure to yield the desired alkoxy omega-substituted iminodicarbonimidic diamide hydrochloride (I). This oil, upon treatment and trituration with anhydrous ether, gives a solid precipitate which may be recrystallized, suitably from ethyl acetate, as the hydrate.

Where reagent (VIII) is a mono omega-substituted dicyandiamide carrying no substitution on the remaining imino nitrogen, then $R^7$ in compound (VIII) is hydrogen and the thus obtained product of formula I will carry no substituents on the $N^2$ and $N^4$ nitrogens, that is to say, $R^6$ and $R^7$ will be hydrogen. Where both nitrogens of the imino groups are substituted, then $R^7$ will be other than hydrogen.

Where it is desired either to place the same substituent on both the $N^2$ and $N^4$ nitrogens or, where $R^7$ is other than hydrogen, to place a different substituent on the $N^2$ nitrogen, the hydrochloride hydrate (I) is suspended in a suitable water immiscible reaction inert organic solvent, suitably ethyl acetate, shaken with an excess of aqueous alkali, suitably aqueous sodium hydroxide, the organic layer separated, dried, and heated under reflux for from about 1 to about 4 hours with an excess of a suitable acylating agent, for example acetyl chloride. After completion of the reaction, the volatile components are removed under reduced pressure to yield the desired $N^2$ acylated compound.

As illustrated above, where $R^7$ has a value selected from the $R^5$ group a different synthetic route is desirable. The methodology is that of Curd, F. H. S, et al *J. Chem Soc.* 1630–45 (1948) and Davidson, J. S., *Chemistry and Industry*, 1977–8 (1965).

The $R^3$ isothiocyanate (XXXI) is added to a suspension of sodium cyanamide in alkanol, such as ethanol, which precipitates the sodium salt of N-cyano-N'-$R^3$thiourea (XXXII) which is filtered off, washed with alkanol. Methyl iodide is added with rapid stirring at ambient temperature. The product separates. The suspension is cooled in an ice bath, the solids filtered off and washed with water and dried to give N-cyano-N'-R³-S-methylisothiourea (XXXIII).

The isothiourea (XXXIII) is added to an alkanolic solution of R⁷ amine and the mixture heated for 4 hours in a pressure bottle at about 50° C. The resulting clear solution is gradually diluted with water (75 cc) and product crystallizes out to give the dicyano R³, R⁷ diamide (XXXIV). This can then be reacted with the hydroxylamine hydrochloride salt (VIII) as described previously to obtain the desired compound (I).

The compounds of the present invention may be made in the form of the monohydrohalic acid addition salts and/or the solvated compound, for example the hydrochloride hydrate or the hydrobromide. Other salts may be made however by simple reaction of a base with acid and may be desirable in order to modify the properties of the product such as its toxicity, taste, physical form or rate of release into the body. For example the compounds may be made in the form of the picrate, saccharinate, acetate, acid maleate, acid phthalate, succinate, phosphate, nitrobenzoate, stearate, mandelate, N-acetyl-glycinate, pamoate, sulfonate, di-sulfonate, cyclohexyl sulphamate, citrate, tartrate, or gluconate.

Stable salts are normally formed with a ratio of one molecule of N, N' poly-substituted imidodicarbonimidic diamides to 1 or 2 molecules of monobasic acid (or more than one molecule of compound 1 in the case of polybasic acids) but the possibility of having basic groups as substituents in $R_5$ for example means that further quantities of acid may be combined with the disubstituted imidodicarbonimidic diamide in some cases. In addition the above molecules may contain various hydrated forms with molecules of water or other solvent included in the molecular formula of the stable entity.

The presence of the imino biguanide nitrogens on the molecule create the possibility of forming acyl derivatives by reaction with appropriate substrates.

There is disclosed an improved mode of prophylaxis and treatment of infections by one or more of Plasmodia; mycobacteria; toxoplasmosis and pneumocystis organisms; and agents causing nocardia infections. The N,N'-substituted asymmetrical biguanides of Formula I of the present invention and/or salts and/or derivatives have antimalarial and antibacterial activity as well as effectiveness against some fungi, protozoans, parasites and viruses. Additionally, the N" and N"' substituted derivatives of formula I exhibit like activities. In particular, these N,N'-substituted asymmetrical biguanides and salts, as well as their N" and N"' substituted derivatives exhibit antiparasitic activity including activity against the Plasmodia of malaria, P. falciparum exhibit antimicrobial activity against mycobacteria including but not limited to M. avium intercellulare, M. avium complex, M. tuberculosis, M. leprae and Toxoplasma gondii and Pneumocystis organisms such as P. carinii associated with but not limited to immunocompromised patients. In addition, these compounds have activity against nocardia infections. These compounds can also be potentiated in combination with sulfonamides or sulfones to improve the biological spectrum and potency of these compounds of Formula I.

Our use data have been confirmed by additional extensive animal studies supported by the U.S. Department of the Army.

It is our finding that the novel compounds of the present invention show high levels of effectiveness when given orally, as compared to the related triazine derivatives which are known to be poorly absorbed. Unlike the related triazine derivatives, this novel series of compounds need not be administered by injection to observe activity comparable to or exceeding other known antimalarial drugs.

EXAMPLES OF BIOLOGICAL ACTIVITY OF THE INVENTION
BIOLOGICAL ACTIVITY AGAINST PLASMODIUM FALCIPARUM

The method of testing for activity against human malaria parasites is described in detail by L. H. Schmidt, *Am. J. Trop. Med. & Hygiene*, 1978, 27:718-737. The detailed methods include all aspects of animal treatment, infection and evaluation of drug efficacy.

The testing is carried out by in vivo screening in a system accepted as the standard for identifying effective antimalarial compounds in humans. The test system utilizes night monkeys (Aotus, Trivergatus) native to Columbia. The monkeys are infected with various selected strains of malaria by means of an intravenous inoculation of $5 \times 10^6$ trophozoites. These trophozoites are obtained directly from P. falciparum infections isolated from humans and the infectious organisms are well characterized with respect to their response to medication. The Aotus system is unique in that it makes possible the evaluation of human falciparum malaria. The drugs are administered to the monkeys via stomach tube, and the usual schedule of testing involves daily dosing of the test animals for seven days. Activity is determined by the clearance or the eradication of the malarial infection.

In Table 1. provided, the activity of title compound JPC7776, N-[3-(2,4,5-trichlorophenoxy)propoxy]-N'-(1-methylethyl)imidodicarbonimidic diamide, is compared to two known antimalarial drugs and is tested comparatively in the highly drug resistant Vietnam Smith strain of Plasmodia falciparum. JPC7776 elicited a clearcut dose response with 8/8 animals treated with 3.0 mg/kg daily for three days showing clearance of parasites (100% response). Three of eight subjects were cured (37.5%). Higher doses produced higher cure rates of 75% and 100% at doses of 30.0 and 150.0 mg/kg. Comparison with proguanil or cycloguanil up to 150 mg/kg for three days showed no activity (0% response).

TABLE 1

| MALARIA STRAIN | DOSE mg/kg | | PRIMARY TREATMENTS | |
|---|---|---|---|---|
| | TOTAL | DAILY | CLEARED | CURED |
| ACTIVITY OF JPC7776 AGAINST PLASMODIUM FALCIPARUM INFECTIONS ||||| 
| Smith | 0.3 | 0.1 | 0/4 | 0/4 |
| | 3.0 | 1.0 | 8/8 | 3/8 |
| | 30.0 | 10.0 | 7/8 | 6/8 1 died early |
| | 150.0 | 50.0 | 3/3 | 3/3 |
| ACTIVITY OF PROGUANIL, AGAINST PLASMODIUM FALCIPARUM INFECTIONS |||||
| Smith | 3.0 | 1.0 | 0/2 | 0/2 |
| | 30.0 | 10.0 | 0/2 | 0/2 |
| | 150.0 | 50.0 | 0/2 | 0/2 |
| ACTIVITY OF CYCLOGUANIL, AGAINST PLASMODIUM FALCIPARUM INFECTIONS |||||
| Smith | 3.0 | 1.0 | 0/2 | 0/2 |
| | 30.0 | 10.0 | 0/2 | 0/2 |
| | 150.0 | 50.0 | 0/2 | 0/2 |

Comparative tests in vivo in mice against Plasmodium have been carried out. Confirming tests conducted under the auspices of the U. S. Department of the Army demonstrate favorable oral activity. Results demonstrate the superior bioavailability and effectiveness of JPC7776 via the oral route as compared to its corresponding triazine WR99210 and the antimalarial proguanil. These data in Table 2 show the number of cures and the effective dose curing 50% of infected animals (ED-50) when drugs were administered in peanut oil via the subcutaneous route (SQ) or when administered as a single oral dose (PO). Premature deaths of animals (earlier than five days post infection) are considered as indications of toxicity. Table 2 summarizes the reduced toxicity of JPC7776 in this screening test and the superior oral efficacy.

A second widely recognized standard test is also presented in Table 3 demonstrating a direct comparison of subcutaneous (SQ) versus oral (PO) dosage of P. Berghei in mice. These tests systems are described in detail in publications by L. Rane and D. S. Rane, 9th Int. Congr. Trop. Med. Malaria. (1973) 1:281 (#406) and (2) T. S. Osdedne, P. B. Russell and L. Rane, J. Med. Chem. 1967. 10:431.

In this methodology, groups of 5 or 10 mice are infected with a standard inoculum of a blood-induced P. berghei infection and are treated with a single subcutaneous dose (9 ng/kg) of test drug suspended in peanut oil or a single oral dose of test drug suspended in hexamethyl cellulose and Tween. The animals are then observed for a maximum of thirty days. Control animals normally live between 6 and 7 days. For a drug to be considered effective, test animals must survive at least twice as long as untreated infected control animals. Animals surviving for thirty days are considered cured.

TABLE 2

ACTIVITY OF JPC7776, TRIAZINE WR99210 AND PROGUANIL AGAINST P. BERGHEI INFECTIONS. COMPARISON OF INJECTED VS. ORAL DOSES

| TEST DRUG | 50% CURE; INJECTED SQ ED-50; MG/KG | 50% CURES: ORAL PO ED-50; MG/KG |
|---|---|---|
| JPC7776 | 498 | 567 (7/10 Cures @ 640) Not Toxic |
| TRIAZINE WR99210 | 245 | No Cures @ 640 |
| PROGUANIL | NO CURES | No Cures, Toxic @ >160 |

TABLE 3

COMPARATIVE ORAL AND SUBCUTANEOUS EFFICACY OF JPC7776 GIVEN TO MICE INFECTED WITH P. BERGHEI: ENHANCED SURVIVAL AND CURES

| | Survival Time (days) | Untreated Survival (days) | Cures (%) | |
|---|---|---|---|---|
| SC Dose; Trial 1 | | | | |
| 40 mg/kg | 11.6 | 6.5 | 0/5 | 0% |
| 160 | n/a (30)* | 6.5 | 5/5* | 100% |
| 640 | 8.0 | 6.5 | 4/5* | 80% |
| SC Dose; Trial 2 | | | | |
| 20 | 7.4 | 6.5 | 0/5 | 0% |
| 40 | 8.8 | 6.5 | 0/5 | 0% |
| 80 | 11.8 | 6.5 | 0/5 | 0% |
| 160 | 16.3* | 6.5 | 2/5* | 40% |
| 320 | n/a (30)* | 6.5 | 5/5* | 100% |
| 640 | n/a (30)* | 6.5 | 5/5* | 100% |
| PO Dose; Trial 1 | | | | |
| 40 | 8.8 | 6.5 | 4/5* | 80% |
| 160 | 15.2* | 6.5 | 0/0 | 0% |
| 640 | 10.0 | 6.5 | 4/5* | 80% |
| PO Dose; Trial 2 | | | | |

TABLE 3-continued

COMPARATIVE ORAL AND SUBCUTANEOUS EFFICACY OF JPC7776 GIVEN TO MICE INFECTED WITH P. BERGHEI: ENHANCED SURVIVAL AND CURES

| | Survival Time (days) | Untreated Survival (days) | Cures (%) | |
|---|---|---|---|---|
| 20 | 7.0 | 6.5 | 0/0 | 0% |
| 40 | 7.4 | 6.5 | 0/0 | 0% |
| 80 | 12.4 | 6.5 | 0/0 | 0% |
| 160 | 15.4* | 6.5 | 0/0 | 0% |
| 320 | 22.5* | 6.5 | 3/5* | 60% |
| 640 | n/a (30) | 6.5 | 5/5* | 100% |

*denotes active with survival greater than 2× controls or cures based on 30 day animal survival.

Table 4 below provides comparative data for the efficacy of JPC7776 against various strains of malaria as tested in vitro with and without a sulfonamide to determine the benefits, if any, of such coadministration with the compounds which are the subject of this invention. The results shown below, measured as the in vitro dose to inhibit 50% growth (ID-50) of the malarial parasites grown in standard culture, (C. S. Genther and C. C. Smith, J. Med. Chem. 1977. 20:237–w243) are presented in nanograms per milliliter (ng/ml). These data show that the intrinsic activity of JPC7776 is potentiated from 4 to 19 fold (see ID-50 values) by sulfonamides in the presence of certain drug resistant parasites.

TABLE 4

POTENTIATION OF JPC7776 BY SULFONAMIDES IN MALARIAL PARASITES INHIBITED IN VITRO. POTENTIATION FACTOR*

| Parasite | JPC776 ID-50 without Sulfamethoxazole (ng/ml) | JPC7776 ID-50 with Sulfamethoxazole (ng/ml) | Factor |
|---|---|---|---|
| African | 19.41 | 4.88 | 4 |
| FCB | 540.81 | 28.46 | 19 |

*Potentiation factor is the ratio of 50% inhibition value (ID-50) of test drug without sulfonamide divided by the ID-50 against the same parasite using an equivalent standard value of sulfonamide.

BIOLOGICAL ACTIVITY AGAINST PNEUMOCYSTIS CARINII

Evaluation of drugs for activity against Pneumocystis carinii is carried out in the widely recognized and well defined testing system developed and published by Dr. Walter T. Hughes. It is widely referred to and is a generally accepted method clearly defined in the literature as to animal maintenance, infection, treatment protocol and evaluation by autopsy and survival of efficacy. A description of the methodology described by W. Hughes et al. is found in Antimicrob. Agents Chemother. 1988, 32:623–625.

In this method rats are immunosuppressed with high doses of glucocorticosteroids while being protected from bacterial infection by concurrent administration of the antibiotic tetracycline. In a standard evaluation animals are immunosuppressed with steroids and various doses of test compounds are administered for six weeks during which time unprotected animals will develop pneumocystis pneumonitis. The percentage of animals free of the disease represents the effectiveness of a selected dose of test drug.

When the animals are immunosuppressed and treated according to the accepted methodology it is normal to observe 75% or more of the test subjects spontaneously developing pneumocystis. A customary method to produce pneumocystis in the animals is to administer 2 mg of dexamethasone and 50 mg tetracycline hydrochloride per liter of drinking water. The test compounds are integrated in the food. For the positive treatment control compound sulfamethoxazole-trimethoprim (SMX/TMP) is fully effective to protect the animals from pneumocystis when given at a dosage of 250 mg/kg SMX in combination with 50 mg/kg of TMP. Another widely used fully effective compound is Dapsone at a dosage of 125 mg/kg.

Table 5 demonstrates the effectiveness of JPC7776 as compared to these known active treatments which are used in treating and preventing pneumocystis infections in humans. JPC 7776 is 100% effective and is effective as Dapsone which is a recommended antipneumocystis drug in humans.

TABLE 5

PREVENTION OF *PNEUMOCYSTIS CARINII* (PCP) INFECTION

| TREATMENT | DAILY DOSE | # TREATED | # INFECTED | EFFICACY |
|---|---|---|---|---|
| JPC7776 | 25 mg/kg | 10/10 | 0/10 | 100% |
| Dapsone | 125 mg/kg | 10/10 | 0/10 | 100% |
| SMX/TMP | 250/50 mg/kg | 10/10 | 0/10 | 100% |
| none | — | 10/10 | 10/10 | 0% |

ACTIVITY AGAINST MYCOBACTERIAL INFECTIONS

Testing of new drugs for activity against Mycobacterial infections is carried out in vitro and in vivo in well defined laboratory procedures which have been widely published. The method used to test for biological activity against growing Mycobacterium avium complex (MAC), Mycobacterium tuberculosis (MTB) and Mycobacterium kanasii (MK) are described by A. H. Gonzalez et al. in *J. Antimicrob. Chemother.* 1989, 24:19–22; S. Majumder and M. H. Cynamon, *Amer. Soc. for Microbiology Mtgs*, U-4, May 1992, abstract.

Activity in vitro was determined against clinical isolates of MAC, MTB and MK using a broth dilution method. Mycobacteria were grown for several days in 7H10 broth, ph 6.6, with 10% OADC enrichment and 0.05% Tween 80. Serial two-fold dilutions of antimicrobial drugs were prepared in 7H10 broth at 128 $\mu$g/ml and less. Cultures containing a final concentration of approximately $2.5 \times 10^4$ to $6.3 \times 10^5$ CFU/ml were incubated on a rotary shaker at 37° C. for 7 days and read where the minimum inhibitory concentration was defined as the MIC at the lowest concentration without visual turbidity. JPC7766 in these studies was compared to known active antimicrobial drugs Proguanil (PG), Cycloguanil (CG), Sulfamethazine (SM) and/or Dapsone (DDS). The results are considered favorable at concentrations below 64 $\mu$g/ml and are shown in Table 6. JPC7776 tests as superior to the other drugs.

TABLE 6

ACTIVITY OF JPC7776 AND OTHER DRUGS AGAINST MYCOBACTERIUM ISOLATES *M. avium* (MAC), *M. tuberculosis* (MTB) and *M. kanasii* (MK).
[Concentrations (MIC), $\mu$g/ml, to inhibit growth in vitro]

| ISOLATE ID | JPC7776 $\mu$g/ml | DDS $\mu$g/ml | PG $\mu$g/ml | CG $\mu$g/ml | SM $\mu$g/ml |
|---|---|---|---|---|---|
| MAC 101 | 16 | 16 | >128 | — | >128 |
| MAC LPR | 32 | 32 | 128 | >128 | 32 |
| MAC FAR | 32 | 64 | 64 | — | 16 |
| MK Picciano | 8 | — | — | 64 | 64 |
| MTB H37Rv | 8 | — | — | 64 | 64 |
| MTB 311 | 16 | — | — | 64 | 64 |

PHARMACEUTICAL COMPOSITIONS

The present invention also provides pharmaceutical compositions comprising as active ingredient a compound according to the present invention together with a pharmaceutically acceptable carrier.

The water solubility of the hydrochloride of the parent compound and most other salts are not very great, so when solutions are required it may often be necessary to add solubilizing agents to the water, choose non-aqueous solvents, or find a more soluble salt or prepare very dilute solutions.

Oral formulations are preferred and this invention has the advantage over related products of being readily absorbed by mammals in sufficient levels to make the compounds of the present invention orally active as therapeutic agents. Formulations for oral or injected use are based on sufficient solubility as to allow the therapeutic agent to enter solution in the stomach or in an injectable medium. The drug formulations will include tablets, pills, capsules, sachets, granules, powders, chewing gums, suspensions, emulsions and solutions: particularly preferred for oral use are tablets and capsules of all varieties and microbe-free solutions for injection or infusion. Where appropriate and necessary the formulations may include diluents, binding agents, dispersing agents, surface-active agents, lubricating agents, coating materials, flavoring agents, coloring agents, controlled release formulations, sweeteners or any other pharmaceutically acceptable additives, for example, gelatin, sodium starch glycolate, lactose, starch, talc, magnesium stearate, microcrystalline cellulose, Povidone, hydrogenated or unsaturated oils, polyglycols, syrups or other aqueous solutions. Where the formulations are tablets or capsules and the like the formulations may be presented as premeasured unit doses or in multidose containers from which the appropriate unit dose may be withdrawn.

The injectable form may be an aqueous or nonaqueous solution, suspension or emulsion in a pharmaceutically acceptable liquid, e.g. sterile pyrogen-free water or parenterally acceptable oils or mixture of liquids which may contain bacteriostatic agents, antioxidants or other preservatives and stabilizers, buffers (preferably but not limited to a physiological pH range of 6.5–7.7, solutes to render the solution isotonic with the blood, thickening agents, suspending agents or other pharmaceutically acceptable additives. Such forms will be presented in unit dose form such as ampules or disposable injection devices or in multi-dose forms such as a bottle from which the appropriate dose may be withdrawn, or as a solid form or concentrate which can be used to quickly prepare an injectable formulation. All formulations for injection are preferable as sterile and pyrogen free. Suppositories containing the compound will also contain suitable carriers, e.g. cocoa butter, polyglycols or other state-of-the-art carriers.

In addition to standard pharmaceutical additives there may be included within formulations of the compound other therapeutic agents, particularly including other antimalarials and antiinfectives.

The preferred dosage range is between 0.5 and 10 mg/kg/day. The range is quite large because the physician must use his judgement on whether the dosage is prophylactic and if given to an infected subject, on what the level of infection is. When given as tablets the tablets may contain 25-250 mg of active material.

EXAMPLE 1

N-[3-(2,4,5-trichlorophenoxy)propoxy]-N'-(1-methylethyl)imidodicarbonimidicdiamide hydrochloride. (XV)

A mixture of 39.5 grams (0.20 mol) of 2,4,5-trichlorophenol and 33 mL of 25% aqueous sodium hydroxide were combined and stirred at ambient temperature for 15 minutes at which time 80 grams (40.7 mL, 0.4 mol) 1,3 dibromopropane were added. The reaction mixture was refluxed for 2 hours at which time an additional 51 mL 14 percent aqueous sodium hydroxide was added and the reaction mixture held at 50°-70° C. for 30 minutes. Upon cooling the lower layer was separated and washed five times with water. The residual organic layer was distilled at 1 mm given several fractions and gave on distillation water and dibromopropane at 30°-40° C., and the product which distilled between 120°-157° C. Fifty grams of a colorless oil was collected which solidified on standing to yield 79% of 3-(2,4,5-trichlorophenoxy) propyl bromide (XII).

Acetohydroxamic acid (8.5 grams, 0.13 mol) was added to 110 mL of an ethanolic solution of sodium hydroxide (4.0 grams, 0.1 mol). The 3-(2,4,5-trichlorophenoxy) propyl bromide (XII) (31.8 grams, 0.1 mol) was added and the mixture refluxed for 6 hours and cooled to room temperature. The solution was filtered and evaporated, the residue dissolved in 100 mL acetone and the solution filtered and concentrated to yield 16.0 grams (51%) of 3-(2,4,5-trichlorophenoxy) propyl acetohydroxamate (XIII), melting point 102°-104° C.

The acetohydroxamate (XIII) (31.3 grams, 0.1 mol) was dissolved in 120 mL of methanol. Hydrochloric acid (30 mL of a 12% solution) was added and the mixture refluxed for 4 hours. The residue was evaporated to dryness under vacuum, washed with dry diethyl ether and recrystallized from isopropyl alcohol (90 mL) giving 15.5 grams (58.7%) 3-(2,4,5-trichlorophenoxy) propyloxy amine hydrochloride (XIV), melting point 158°-168° C.

The hydroxylamine hydrochloride (XIV) (10 grams, 0.0267 mol) in 160 mL ethanol was treated with 6N aqueous HCl until the solution was acidic. Isopropyl dicyanodiamide (4.4 grams, 0.0347 mol) was added and the mixture heated at reflux for 4 hours at which time the solvent was evaporated off. The resulting solid material was soluble in water and ethyl acetate and the resulting oil was treated with anhydrous ether to give a solid precipitate that was filtered, washed with ether and dried. The resulting white solid, recrystallized from ethyl acetate after charcoaling yielded 2.0 grams of the titled compound (XV) as a monohydrate with a melting point of 100° C.;

In accordance with the above procedure but where, in place of 1,3-dibromopropane there is utilized methylene dibromide, 1,2-dibromoethane, 1,4-dibromobutane or 1,5-dibromopentane there is obtained the corresponding methoxy, ethoxy, butoxy or pentoxy analogue respectively.

In accordance with the above procedure but where, in place of 1,3-dibromopropane there is utilized 1,2-dibromopropane, 1,3-dibromo-2-methoxypropane, 1,4-dibromo-2-ethoxybutane or 1,5-dibromo-3-ethoxypentane there is obtained the corresponding 2-methylethyl, 2-methoxypropoxy, 2-ethoxybutoxy or 3-ethoxypentoxy analogue respectively.

EXAMPLE 2

N-[3-(2,5-dichlorothiophenoxy)propoxy]-N'-(1-methylethyl)imidodicarbonimidic diamide hydrochloride. (XVII)

In similar fashion to the synthesis of (XV) 2,5-dichlorothiophenol (35.8 grams, 0.2 mol) was treated with sodium hydroxide (40 mL of 20% aqueous solution) and then combined with 1,3-dibromopropane (160 grams, 0.8 mol) and refluxed for 4 hours. The mixture was cooled, the aqueous layer separated and neutralized with 20% sodium hydroxide solution, and the lower layer washed five times with water and distilled at 1 mm Hg. The main fraction was collected between 130°-145° C. as a colorless oil (50 grams, 84%) of 2,5-dichlorothiophenoxy propyl bromide (XVI) is further reacted with acetohydroxamic acid as described previously in Example 1 and hydrolyzed to give the 3-(2,5-dichlorothiophenoxy)propyloxamine hydrochloride (XVII) which is then reacted with isopropyl dicyanodiamide as described previously in Example 1 to give the title compound (XVIII).

In accordance with the above procedure but where, in place of 2,5-dichlorothiophenol, there is utilized n-propyl mercaptan, cyclohexyl mercaptan, and 3-tetrahydropyranol there is obtained the corresponding N-3-(1-propylthio-, cyclohexylthio-, and N-3-tetrahydropyranyloxy)propyloxy-N'-(1-methylethyl) imidodicarbonimidic diamide hydrochloride.

EXAMPLE 3

N-3-(4-chlorothiophenoxy)propyloxy-N'-(1-methylethyl)imidodicarbonimidic diamide hydrochloride (XXI)

In similar fashion to the synthesis of (XV), 4-chlorothiophenol (28.9 grams, 0.2 mol) was treated with sodium hydroxide (40 mL of 20% aqueous solution) and then combined with 1,3-dibromopropane (160 grams, 0.8 mol) and refluxed for 4 hours. The mixture was cooled, the aqueous layer separated and neutralized with 20% sodium hydroxide solution, and the lower layer washed five times with water and distilled at 1 mm Hg. The main fraction was collected between 120°-130° C. as a colorless oil (47.5 grams, 90%) which crystallized on standing to give 4-chlorothiophenoxy propyl bromide (XIX) is then further reacted with acetohydroxamic acid as described previously in Example 1 and hydrolyzed to give the 3-(4-chlorothiophenoxy)-propyloxamine hydrochloride (XX). This in turn is reacted with isopropyl dicyanodiamide as described previously in Example 1 to give the title compound (XXI).

In accordance with the above procedure but where, in place of isopropyl dicyanodiamide, there is utilized N''-phenyl-N-isopropyl dicyanodiamide or other N''-substituent such as methyl, ethyl or phenylmethyl, there is obtained the corresponding N-3-(4-chlorothiophenoxy) propoxy N'''-phenyl or methyl, ethyl or phenylethyl, N'-(1-methylethyl)imidodicarbonimic diamide hydrochloride.

Where it is desired to form the N", N"'-dialkanoyl or respective monoalkanoyl derivatives of the foregoing unsubstituted derivatives in FIG. 1, the latter are treated in the manner set forth in Example 4 below, such that an appropriate 1:1 molar ratio or an acid chloride or anhydride for mono-substituted or 2:1 molar ratio for the disubstituted derivatives allows the product to be obtained.

EXAMPLE 4

N"-acetyl-N-3-(2,4,5-trichlorophenoxy)propoxy]-N'-(1-methylethyl) imidodicarbonimidic diamide hydrochloride (XXII).

N-[2-(2,4,5-trichlorophenoxy) propoxy]-N'-(1-methylethyl)imidodicarbonimidic diamide hydrochloride hydrate (XV) (1.0 gram, 0.002 mol) was suspended in ethyl acetate (20 mL) and shaken with 0.1 mL of 25% aqueous sodium hydroxide solution. The organic layer was separated and dried (magnesium sulfate), 0.1 mL of acetyl chloride added and the mixture refluxed for 2 hours. The subsequent mixture was concentrated to give 0.5 grams (47%) of the title compound (XXII) as white crystals, melting point 160°-170° C.

EXAMPLE 5

N-[3-(2,4,5-trichlorophenoxy) ethoxy]-N'-(1-methylethyl)imidodicarbonimidic diamide hydrochloride (XXVI)

A mixture of 39.5 grams (0.20 mol) of 2,4,5-trichlorophenol was dissolved in 40 mL of 20% aqueous sodium hydroxide and added dropwise to refluxing dibromoethane (85.8 mL, 1 mol) over 1 hour. The mixture was refluxed for 2 hours and allowed to cool to room temperature. Upon cooling the lower layer was separated and washed four times with water. The residual organic layer was distilled at 1 mm to give the main fraction between 145°-155° C. as colorless oil (51.4 grams, 85%) which was 2-(2,4,5-trichlorophenoxy) ethyl bromide (XXIII).

The trichlorophenoxy ethyl bromide (XXIII) (30.4 g, 0.1 mol) was added to acetohydroxamic acid (8.5 grams, 0.13 mol) in 110 mL of ethanolic sodium hydroxide (4.0 grams, 0.1 mol) as described previously in Example 1 and the mixture refluxed for 6 hours, cooled to room temperature, filtered, the ethanol evaporated and the residue dissolved in acetone (100 mL) the solution filtered and concentrated to yield 19.2 grams (68%) of 2-(2,4,5-trichlorophenoxy) ethyl acetohydroxamate (XXIV), melting point 160°-162° C.

The acetohydroxamate (XXIV) was hydrolyzed to the 2-(2,4,5-trichlorophenoxy) ethoxy amine hydrochloride (XXV) as described for the corresponding propyl acetohydroxamate (XIII). The ethoxyamine hydrochloride was reacted with isopropyl dicyanodiamide as previously described in Example 1 to give the N-[2-(2,4,5-trichlorophenoxy) ethoxy]-N'-(1-methylethyl)imidodicarbonimidic diamide hydrochloride (XXVI).

EXAMPLE 6

N-(2,4,5-trichlorobenzoxy)-N'-(1-methylethyl-)imidodicarbonimidic diamide hydrochloride (XXX)

2,4,5-Trichlorobenzyl bromide (XXVII) (16.1 g, 0.1 mol) is added to acetohydroxamic acid (8.5 grams, 0.13 mol) in 110 mL of ethanolic sodium hydroxide (4.0 grams, 0.1 mol) as described previously in Example 1 and the mixture refluxed for 6 hours, cooled to room temperature and filtered. The ethanol evaporated and the residue dissolved in acetone (100 mL) the solution filtered and concentrated to yield 2-(2,4,5-trichlorobenzyl)acetohydroxamate (XXVIII).

The acetohydroxamate (XXVIII) is hydrolyzed to the 2,4,5-trichlorobenzoxy amine hydrochloride (XXIX) as described for the corresponding propyl acetohydroxamate (XIII). The benzoxyamine hydrochloride (XXIX) was reacted with isopropyl dicyanodiamide as previously described in Example 1 to give the N-(2,4,5-trichlorobenzoxy)-N'-(1-methylethyl-)imidodicarbonimidic diamide hydrochloride (XXX).

EXAMPLE 7

N-3-(2,4,5-trichlorophenoxy)propoxy-N'-(p-chlorophenyl)-N"-methyl-imidodicarbonimidic diamine (XXVa).

p-Chlorophenyl isothiocyanate (XXXIa) (50.7 grams) is added to a suspension of sodium cyanamide (19.2 g) in ethanol (30 mL) with stirring which slowly dissolves and precipitates the sodium salt of N-cyano-N'-p-chlorophenylthiourea (XXXIIa) which is filtered off, washed with ethanol and dried to yield 36.2 grams which are suspended in 200 mL of ethanol and combined with 37.6 grams of methyl iodide with rapid stirring at ambient room temperature. The product separates as heat is evolved. The suspension is cooled in an ice bath, the solids filtered, washed with water and dried to give N-cyano-N'-p-chlorophenyl-S-methylisothiourea (XXXIIIa).

In accordance with the above procedure but where in place of p-chlorophenyl isothiocyanate there is utilized the corresponding methyl, ethyl, iso-propyl, propyl and benzyl derivative, there is obtained the corresponding N-cyano-N'-methyl, ethyl, iso-propyl, propyl and benzyl-S-methylisothiourea.

The S-methylisothiourea (XXXIIIa) prepared as above is added to an ethanolic solution of methylamine (79.4 mL containing 4.2 g methylamine) and the mixture heated for 4 hours in a pressure bottle at 50° C. The resulting clear solution was gradually diluted with water (75 cc) and product crystallizes out, is filtered off to give the desired dicyanodiamide (XXXIVa).

In accordance with the above procedure but where in place of methylamine there is utilized the corresponding phenyl, ethyl, iso-propyl, propyl and benzyl amine, there is obtained the corresponding dicyan-N'-phenyl, ethyl, iso-propyl, propyl and benzyl diamide.

The dicyanodiamide (XXXIVa) is then reacted with N-3-(2,4,5-trichlorophenoxy) propoxyamine hydrochloride (XIV) as described previously in Example I to yield the title compound.

EXAMPLE 8

Pharmaceutical Composition

Tablets of
N-[3-(1,4,5-trichlorophenoxy)propoxy]-N'-(1,3-methylethyl)-imidodicarbon imidic diamide hydrochloride hydrate.

One tablet contains 25 mg-500 mg of active ingredient depending upon the specific organism being treated, due to differential sensitivity of the infectious microbe.

| | 25 mg. | 50 mg. | 100 mg. | 250 mg. | 500 mg. |
|---|---|---|---|---|---|
| active ingredient | 25 mg. | 50 mg. | 100 mg. | 250 mg. | 500 mg. |
| microcrystalline cellulose | 100 mg. | 150 mg. | 200 mg. | 250 mg. | 300 mg. |
| Povidone K 29-32 | 10 mg. | 25 mg. | 25 mg. | 50 mg. | 75 mg. |
| Sodium starch glycolate | 20 mg. | 30 mg. | 40 mg. | 50 mg. | 60 mg. |
| Magnesium stearate | 3 mg. | 5 mg. | 8 mg. | 10 mg. | 13 mg. |
| TOTAL WEIGHT | 158 mg. | 260 mg. | 373 mg. | 610 mg. | 948 mg. |
| 100,000 Tablets | 15,800 g. | 26,000 g. | 37,000 g. | 61,000 g. | 94,800 g |

The formulation is for production of 100,000 tablets (15.8-94.8 kg). The tablets will be coated with hydroxypropyl methylcellulose, color, titanium dioxide, polyethylene glycol 6000 and Carnuba Wax to approximate weight 2-5% of the tablet weight.

We claim:

1. A compound of the formula

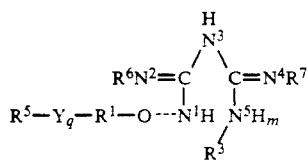

wherein:

$R^1$ is substituted or unsubstituted divalent aliphatic group of 1 to 16 carbon atoms; wherein the substituents are mono or poly and are selected from the group consisting of lower alkyl, aryl and aralkyl, $R^3$ is selected from the group consisting of same group of values as $R^5$ other than carbocycloaryl, and when further bonded to the nitrogen to which it is attached, a saturated heterocycle of 4-8 carbon atoms, $R^5$ is selected from the group consisting of substituted and unsubstituted alkyl of 1-10 carbon atoms, cycloalkyl, heterocycloalkyl of 3-8 carbon atoms, mono and polycarbocycloaryl of 4-7 atoms per ring, wherein the substituents are;

mono or poly and are selected from the group consisting of lower alkyl, halo lower alkyl, cycloalkyl of 3-8 carbon atoms, lower alkenyl, lower alkynyl, nitro, lower alkoxy, lower alkoxy-carbonyl, phenyl loweralkyl, phenyl, mono and polyhalophenyl, phenoxy, mono and polyhalophenoxy;

and halo provided however, that such halo substitution is in a mono and polycarbocycloaryl of 4-7 atoms per ring, $R^6$ and $R^7$ which may be the same or different are hydrogen, alkanoyl or alkoxy alkanoyl, and when further bonded to the nitrogen to which either is attached, a saturated heterocycle of 4-8 carbon atoms, and $R^7$ may also be selected from the group consisting of same group of values as $R^5$, and when further bonded to the nitrogen to which it is attached, a saturated or unsaturated heterocycle of 4-8 carbon atoms, Y is oxygen or sulfur, q is 0 or 1, m is 1 or 0, having the latter value where $R^3$ is a moiety having two bonds attached to $N^5$, provided that unless otherwise stated the prefix alk designates moieties which are straight chain or branched chain of 1-24 carbon atoms, and when further prefixed by the term lower, designates 1-6 carbon atoms, the respective tautomers thereof, the pharmaceutically acceptable salts and addition salts thereof and the hydrates of said salts and addition salts and mono and diacyl derivatives thereof.

2. The compound of claim 1 wherein:

$R^5$ is selected from the group consisting of substituted and unsubstituted methyl, ethyl, n-propyl, isopropyl, n-butyl, isobutyl, n-pentyl, isopentyl and n-decyl, phenyl, benzyl, phenethyl, phenylpropyl, cyclopentyl, cyclohexyl, cycloheptyl and methylcyclohexyl, wherein the substituents are;

mono or poly and are selected from the group consisting methyl, ethyl, cyclohexyl, cyclopentyl and cycloheptyl; di- and tri halophenyl, di- and tri halophenoxy; and halo provided however, that such halo substitution is in an aryl moiety.

3. The compound of claim 1 wherein $R^3$ is substituted and unsubstituted straight or branched chain alkyl of 1 to 10 carbon atoms.

4. The compound of claim 1 wherein $R^3$ is joined with the $N^5$ to form, a saturated heterocycle of 4 to 8 carbon atoms.

5. The compound of claim 1 wherein the $R^5$ moiety is unsubstituted and is selected from the group consisting of methyl, ethyl, n-propyl, iso-propyl, isobutyl, n-pentyl, n-decyl, cyclopentyl, cyclohexyl, cycloheptyl and phenyl.

6. The compound of claim 1 wherein the substituents on the $R^5$ moiety may be mono or poly substituents and are selected from the group consisting of:

methyl, ethyl, cyclopentyl, cyclohexyl, cycloheptyl, nitro, methoxy, ethoxy, propoxy, benzyl, phenethyl, biphenylenyl; and chloro, bromo and fluoro, provided however said halo substitutions occurs only on an aryl moiety.

7. The compound of claim 1 wherein the $R^3$ moiety is substituted and said substituents are mono or poly substituents and are selected from the group consisting of:

methyl, ethyl, cyclopentyl, cyclohexyl, cycloheptyl, methoxy, ethoxy, propoxy, benzyl, phenethyl, biphenylenyl.

8. The compound of claim 3 wherein $R^3$ is selected from the group consisting of methyl, ethyl and iso-propyl.

9. The compound of claim 3 wherein $R^3$ is substituted and the substituents are selected from the group consisting of alkoxy of 1-6 carbon atoms.

10. The compound of claim 1 of the formula

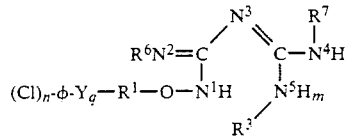

wherein:

φ is a substituted phenyl, n is an integer of 1–4, Y is O, $R^1$ is $(CH_2)_z$ where z is an integer of 1–4 and $R^3$ is isopropyl, its tautomers, a non-toxic acid addition salt, or a mono or diacetyl derivative thereof.

11. The compound of claim 1 which is N-[3-(2,4,5-trichlorophenoxy) propoxy]-N'-(1-methylethyl)imidodicarbonimidic diamide, its tautomers, a non-toxic acid addition salt, or a mono or diacetyl derivative thereof.

12. The compound of claim 1 which is N-[3-(2,5-dichlorothiophenoxy) propoxy]-N'-(1-methylethyl)imidodicarbonimidic diamide, its tautomers, a non-toxic acid addition salt, or a mono or diacetyl derivative thereof.

13. The compound of claim 1 which is N-3-(4-chlorothiophenoxy) propoxy-N'-(1-methylethyl)imidodicarbonimidic diamide, its tautomers, a non-toxic acid addition salt, or a mono or diacetyl derivative thereof.

14. The compound of claim 1 which is N-3,4-dichlorobenzoxy -N'-(1-methylethyl)imidodicarbonimidic diamide, its tautomers, or a non-toxic acid addition salt or a mono or diacetyl derivative thereof.

15. A method of protecting subjects liable thereto from infections caused by an organism selected from the group consisting of Plasmodium sp., Mycobacterium sp and *Pneumocystis carinii* which comprises administering to a subject liable to infection by exposure to such organisms, a prophylactically effective amount of a compound of claim 1.

16. A method of claim 15 wherein the organisms are selected from the group consisting of *P. falciparum, M. avium* complex, *M. tuberculosis* and *M. Kanasii.*

17. A method of reducing the level of infection in subjects suffering therefrom caused by an organism selected from the group consisting of Plasmodium sp., Mycobacterium sp and *Pneumocystis carinii* which comprises administering to an infected subject an infection reductively effective amount of a compound of claim 1.

18. A method of claim 17 wherein the organisms are selected from the group consisting of *P. falciparum, M. avium* complex, *M. tuberculosis* and *M. Kanasii.*

19. A prophylactic composition for protecting subjects liable thereto from infections caused by an organism selected from the group consisting of Plasmodium sp., Mycobacterium sp. and *Pneumocystis carinii* which comprises a prophylactically effective amount of a compound of claim 1 and a pharmaceutically acceptable carrier.

20. A composition of claim 19 wherein the organisms are selected from the group consisting of *P. falciparum, M. avium* complex, *M. tuberculosis* and *M. Kanasii.*

21. A composition for reducing the level of infection in subjects suffering from infections caused by an organism selected from the group consisting of Plasmodium sp., Mycobacterium sp. and *Pneumocystis carinii* which comprises an infection reductively effective amount of a compound of claim 1 and a pharmaceutically acceptable carrier.

22. A composition of claim 21 wherein the organisms are selected from the group consisting of *P. falciparum, M. avium* complex, *M. tuberculosis* and *M. Kanasii.*

23. A composition of claim 19 formulated for oral administration.

24. A composition of claim 21 formulated for oral administration.

25. A composition of claim 23 formulated for administration as tablets or capsules.

26. A composition of claim 24 formulated for administration as tablets or capsules.

27. A method of potentiating the method of claim 15 which comprises the coadministration with sulfonamides or sulfones.

28. A method of potentiating the method of claim 17 which comprises the coadministration with sulfonamides or sulfones.

29. The compound of claim 11 which is N-[3-(2,4,5-trichlorophenoxy) propoxy]-N'-(1-methylethyl)imidodicarbonimidic diamide hydrochloride mono hydrate and its tautomers.

30. The compound of claim 1 which is N"-acetyl-N-[3-(2,4,5-trichlorophenoxy) propoxyl]-N'-(1-methylethyl)imidodicarbonimidic diamide, its tautomers, a non-toxic acid addition salt, or a mono or diacetyl derivative thereof.

31. The compound of claim 1 which is N-[3-(2,4,5-trichlorophenoxy) ethoxyl]-N'-(1-methylethyl)imidodicarbonimidicdiamide, its tautomers, a non-toxic acid addition salt, or a mono or diacetyl derivative thereof.

32. The compound of claim 1 wherein $R^3$ is selected from the group consisting of methyl, ethyl, n-propyl, iso-propyl, isobutyl, n-pentyl, n-decyl, cyclopentyl, cyclohexyl, methylcyclohexyl, cycloheptyl, benzyl, phenethyl, phenylpropyl tetrahydrofuranyl, pyrrolidinyl, piperidyl and morpholinyl, and also forms, with the nitrogen to which it is attached, a saturated heterocycle of 4–8 carbon atoms selected from the group consisting of pyrrolino, piperidino or pyrrolidino.

* * * * *